United States Patent
Kim et al.

(10) Patent No.: US 9,976,161 B2
(45) Date of Patent: May 22, 2018

(54) REACTOR FOR CONTINUOUS SACCHARIFICATION OF HIGH-SOLID BIOMASS

(71) Applicants: SK Innovation Co., LTD., Seoul (KR); SK Energy Co., LTD., Seoul (KR)

(72) Inventors: Taewan Kim, Daejeon (KR); Minsu Koo, Daejeon (KR); Younghwan Chu, Daejeon (KR); Donghyun Kim, Daejeon (KR); Taeseung Kim, Yongin-si (KR); Bonwook Koo, Daejeon (KR); Minji Sung, Seoul (KR)

(73) Assignees: SK Innovation Co., Ltd., Seoul (KR); SK Energy Co., Ltd., Seoul (KR)

( * ) Notice: Subject to any disclaimer, the term of this patent is extended or adjusted under 35 U.S.C. 154(b) by 145 days.

(21) Appl. No.: 14/683,037

(22) Filed: Apr. 9, 2015

(65) Prior Publication Data

US 2015/0291989 A1 Oct. 15, 2015

(30) Foreign Application Priority Data

Apr. 9, 2014 (KR) .................. 10-2014-0042623

(51) Int. Cl.
| | |
|---|---|
| *C12M 1/00* | (2006.01) |
| *C12M 3/00* | (2006.01) |
| *C12P 19/14* | (2006.01) |
| *C12M 1/40* | (2006.01) |
| *C12M 1/06* | (2006.01) |

(Continued)

(52) U.S. Cl.
CPC ............ *C12P 19/14* (2013.01); *C12M 21/12* (2013.01); *C12M 21/18* (2013.01); *C12M 27/02* (2013.01); *C12M 27/22* (2013.01); *C12M 29/06* (2013.01); *C12M 41/12* (2013.01); *C12M 41/26* (2013.01); *C12P 19/02* (2013.01); *C12P 7/10* (2013.01)

(58) Field of Classification Search
CPC ...... C12M 27/18; C12M 25/06; C12M 29/06; C12M 27/22
See application file for complete search history.

(56) References Cited

U.S. PATENT DOCUMENTS

| | | | | |
|---|---|---|---|---|
| 4,212,949 A | * | 7/1980 | Kozhemyakin | ........ C12M 23/04 435/294.1 |
| 4,378,434 A | * | 3/1983 | Prentice | ................. C12M 27/02 435/157 |

(Continued)

FOREIGN PATENT DOCUMENTS

| | | |
|---|---|---|
| EP | 0011870 A1 | 6/1980 |
| JP | 11-226377 A | 8/1999 |

(Continued)

OTHER PUBLICATIONS

Office Action dated Jun. 21, 2016 of corresponding Korean Patent Application No. 10-2015-0034398—8 pages.

(Continued)

*Primary Examiner* — Nathan A Bowers
(74) *Attorney, Agent, or Firm* — The Webb Law Firm

(57) ABSTRACT

A reactor for continuous saccharification of biomass having a high solid content comprises perforated plates and stirring means, in which the perforated plates includes nozzles for feeding additives, including a saccharification enzyme, and a sensor, which communicate with the holes of the perforated plates.

10 Claims, 2 Drawing Sheets

(51) Int. Cl.
*C12M 1/34* (2006.01)
*C12P 19/02* (2006.01)
*C12P 7/10* (2006.01)

(56) References Cited

U.S. PATENT DOCUMENTS

| | | | |
|---|---|---|---|
| 4,409,329 A | 10/1983 | Silver | |
| 4,654,308 A * | 3/1987 | Safi | C02F 3/2806 312/209 |
| 4,840,905 A * | 6/1989 | Kearns | B01F 7/00641 261/84 |
| 5,605,834 A * | 2/1997 | Eberthson | C05F 17/0205 435/290.3 |
| 5,795,732 A * | 8/1998 | Schilling | C12M 27/22 366/295 |
| 5,955,326 A * | 9/1999 | Bungay, III | C12P 19/04 435/101 |
| 6,197,573 B1 | 3/2001 | Suryanarayan et al. | |
| 8,617,480 B2 | 12/2013 | Funaoka et al. | |
| 2012/0171718 A1 | 7/2012 | Le et al. | |
| 2013/0059339 A1 * | 3/2013 | Karerangabo | C12M 23/22 435/70.1 |

FOREIGN PATENT DOCUMENTS

| | | |
|---|---|---|
| JP | 2003-236355 A | 8/2003 |
| KR | 10-2009-0103643 A | 10/2009 |
| KR | 10-2010-0130979 A | 12/2010 |
| KR | 10-2013-0097582 A | 9/2013 |
| WO | 2009/068875 A1 | 6/2009 |

OTHER PUBLICATIONS

Office Action dated Mar. 4, 2016 of corresponding Australian Patent Application No. 2015201767—5 pages.

* cited by examiner

REACTOR FOR CONTINUOUS SACCHARIFICATION OF HIGH-SOLID BIOMASS

CROSS REFERENCE TO PRIOR APPLICATION

This application claims priority to Korean Application No. 10-2014-0042623 filed on Apr. 9, 2014.

TECHNICAL FIELD

The present disclosure relates to a reactor for continuous saccharification of biomass having a high solid content.

BACKGROUND ART

Biofuel production processes of preparing bioethanol from cellulose are grossly divided into feedstock acquisition, pretreatment, saccharification, fermentation and purification processes. Particularly, the pretreatment process is indispensable when non-degradable woody biomass composed of cellulose, hemicellulose and lignin, linked in a complex and hard form, is used. The pretreatment process aims to effectively separate cellulose and hemicellulose from lignin having a complex and hard structure, and the separated cellulose is hydrolyzed into glucose, a representative monosaccharide, by three enzymes, i.e., endo-$\beta$-1,4-glucanase) [EC 3.2.1.4], exo-$\beta$-1,4-glucanase [EC 3.2.1.91], and $\beta$-glucosidase (EC 3.2.1.21) in the saccharification process. When glucose is fermented, ethanol is produced.

A technology for enzymatic hydrolysis of cellulose and hemicellulose has been known long ago, but has disadvantages in that high catalyst costs are required, the reaction proceeds slowly, and high equipment investment is required due to the need for a large-sized reactor. In addition, when a large amount of an enzyme is used, the rate of saccharification can increase, but cost problems arise, and there is a limit to increasing the efficiency of saccharification, due to the inhibitory action of a reaction substrate and a reaction product. However, in this case, the extreme reaction conditions of high temperatures and high pressures are not required, no toxic byproducts are produced, and the consumption of energy is reduced. Thus, there is a high need for the development of a technology for saccharifying biomass using an enzyme.

In order to achieve the commercialization of cellulosic ethanol, cellulosic ethanol should be produced at a concentration of 5% (w/w) so that ethanol can be separated by distillation using a small amount of energy. For this purpose, a saccharification liquid having a sugar content of 11% (w/w) or more based on ethanol (theoretical yield: 0.51, and actual fermentation efficiency: 90%) should be produced. After pretreatment, the enzymatic saccharification of biomass having a solid content of about 15-20% (sugar content: 50-70%) should be started.

However, biomass having a solid content of 15-20% is in a state similar to kneaded clay or soybean paste, in which the movement of a fluid in the biomass substrate hardly occurs. Thus, it is not easy to distribute a saccharification enzyme uniformly in the biomass substrate having this solid content or to maintain a reaction temperature suitable for saccharification. In addition, because the pH of the saccharification liquid is reduced due to the dissociation of acetyl groups present in the biomass during the saccharification process, a basic substance (e.g., NaOH) should be continuously fed during the reaction, but is difficult to mix, and thus makes it difficult to maintain an effective saccharification reaction.

For the efficient mixing of biomass, a variety of stirred tank reactors have been developed, which perform fine crushing by perforated plates and mixing by stirring means.

EP 0011870A1 discloses a stirred tank reactor for mixing a solid material and a liquid material, which comprises fixed perforated plates and stirring means. U.S. Pat. No. 8,617,480B2 discloses a stirred tank reactor, which comprises fixed perforated plates and stirred means together with an injection nozzle disposed in a space defined by the perforated plates. U.S. Pat. No. 4,409,329A discloses mixing biomass using perforated plates, and is characterized in that the distance between the perforated plates for mixing of biomass having a high solid content is as extremely narrow as 5 cm or less and in that an additive is introduced through an inlet hole provided in the upper portion of the stirred tank reactor.

The discussion in the foregoing background section is to provide general background information, and does not constitute an admission of prior art.

SUMMARY

One aspect of the present invention provides a reactor for continuous saccharification, which comprises nozzles for feeding additives, including a saccharification enzyme, to the inside of perforated plate holes, and a sensor, and in which the saccharification enzyme can be efficiently mixed so that biomass having a high solid content can be efficiently saccharified.

Another aspect of the present invention provides a method of saccharifying high-viscosity biomass using the reactor for continuous saccharification.

Still another aspect of the present invention provides a reactor for continuous saccharification of high-viscosity biomass, which comprises: (a) a rotary shaft that is rotatable by separate power; (b) a plurality of stirring means fixed to the rotary shaft; (c) a cylindrical saccharification unit in which the rotary shaft passes through the central portion of the saccharification unit and the plurality of stirring means fixed to the rotary shaft are disposed at predetermined distances from one another; and (A) a plurality of perforated plates disposed between the stirring means in the cylindrical saccharification unit and configured to define a space including each of the stirring means, each of the perforated plates including one or more flow channels formed to extend from the outer circumferential surface of the perforated plate to the inside of the holes of the perforated plate, and nozzles fluidically communicating with the flow channels and the inside of the holes and configured to feed an additive.

A further aspect of the present invention also provides a method of continuous saccharification of high-viscosity biomass, the method comprising the steps of: (a) feeding an additive to the biomass through a nozzle fluidically communicating with the inside of the hole of the perforated plate by rotating a stirring means above each of perforated plates in a saccharification unit to allow biomass to reach the perforated plate, and mixing the additive with the biomass by rotation of a stirring means disposed under the perforated plate while passing the biomass through the hole while; and (b) saccharifying the biomass by moving the biomass downward in the saccharification unit while repeating step (a) by the perforated plates and stirring means sequentially disposed in the saccharification unit, wherein the additive that is fed through the nozzle are at least one selected from an enzyme, an acidic or basic substance for pH adjustment and a surfactant, which are fed through different nozzles.

EXPLANATION OF SYMBOLS

Figure 1:
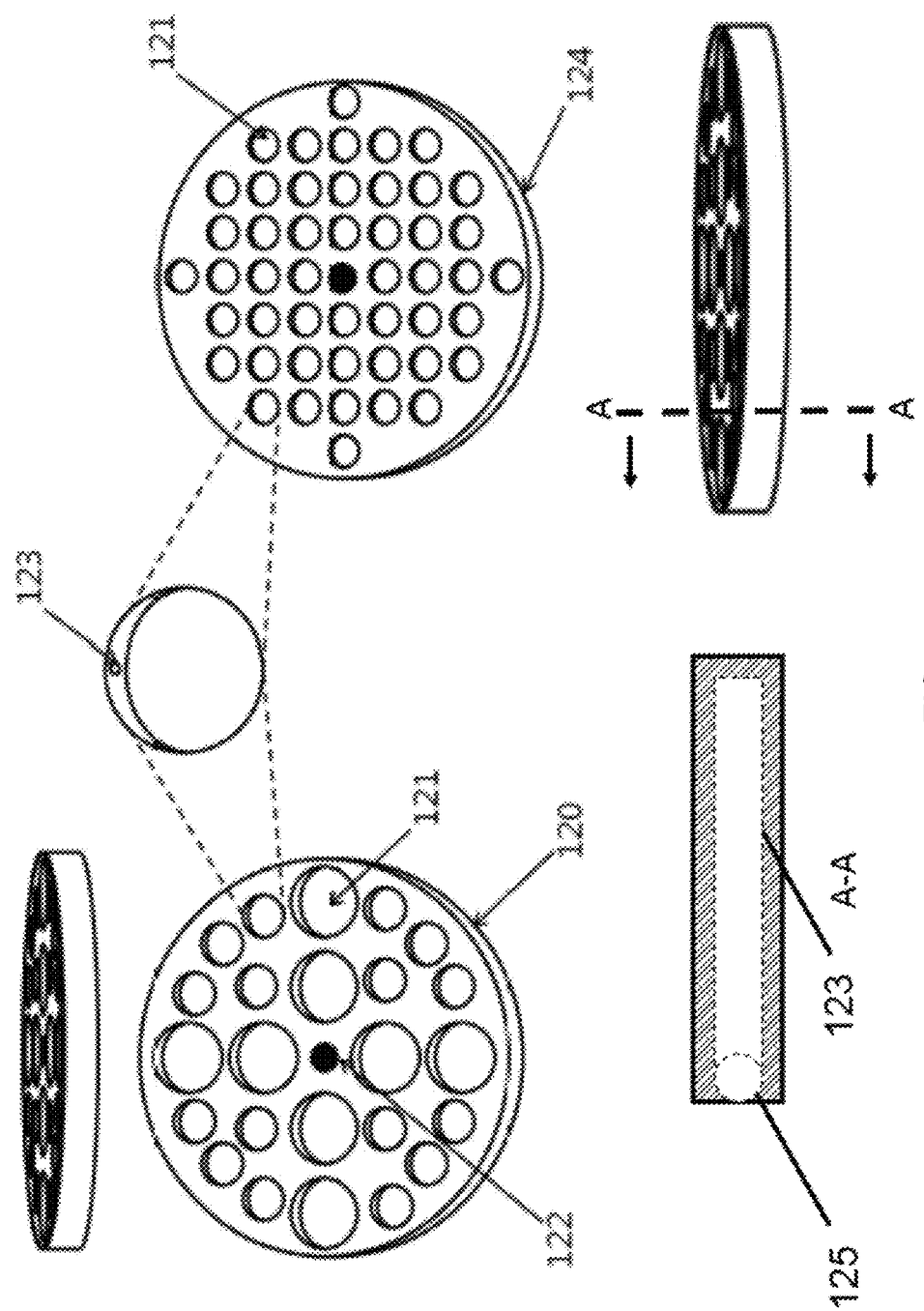
FIG. 1 is a schematic view showing the structure of perforated plates, which are mounted in a reactor for continuous saccharification of high-viscosity biomass, and holes formed in the perforated plates.
Figure 2:
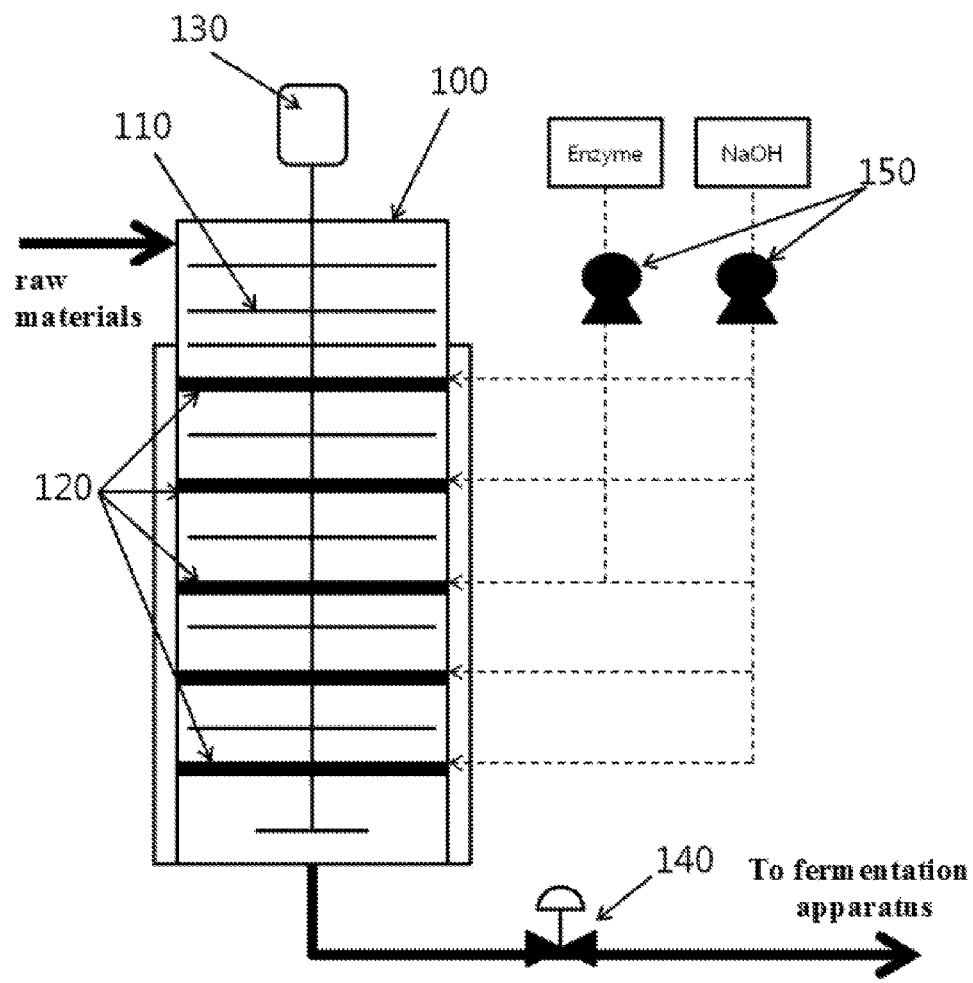
FIG. 2 is a conceptual view of a reactor for continuous saccharification of high-viscosity biomass, which comprises additive feeding units and a low-viscosity saccharification unit.

100: reactor for continuous saccharification of high-viscosity biomass
110: stirring means
120: upper perforated plate
121: hole
122: rotary shaft
123: flow channel
124: lower perforated plate
125: nozzle
130: motor for the reactor
140: valve
150: additive pump

EMBODIMENTS

In the enzymatic saccharification reaction of biomass having a solid content of 10-30%, which is performed prior to ethanol fermentation, there may be problems in terms of the efficiency of saccharification, because the movement of a fluid into the biomass hardly occurs so that it will be difficult to mix an enzyme by simple stirring and maintain saccharification temperature and pH.

The present inventors have paid attention to a continuous saccharification reactor in which additives, including a saccharification enzyme, an acidic or basic substance for pH adjustment, buffer and a surfactant, are injected into the holes of perforated plates that finely crush high-viscosity biomass, in order to increase the efficiency of mixing of an enzyme required for increasing the efficiency of saccharification of high-viscosity biomass. In other words, the present inventors have developed a continuous saccharification reactor in which high-viscosity biomass passes sequentially through perforated plates and stirring means while a saccharification enzyme is uniformly and rapidly dispersed on the biomass, and at the same time, the biomass is crashed finely by the holes of the perforated plates and the stirring means while the mixing of the enzyme and an additive with the biomass is repeated to ensure the efficient mixing of the enzyme, thereby increasing the efficiency of saccharification.

In one example of stirred tank reactor for mixing a solid material and a liquid material, which comprises fixed perforated plates and stirring means, because a hole for injecting the liquid material is disposed in the upper or lower portion of the reactor, a long stirring time is required for uniform mixing.

In another example of a stirred tank reactor, which comprises fixed perforated plates and stirred means together with an injection nozzle disposed in a space defined by the perforated plates, because the nozzle is mounted on the inner wall surface of the stirred tank reactor, it is not easy to mixing an introduced material with biomass stagnant in the cavity of the reactor.

Taken together, a variety of stirred tank reactors may comprise perforated plates and stirring means. However, because a nozzle for feeding an additive is disposed on the wall surface or in the upper or lower portion of the stirred tank reactor, an enzyme and an additive such as an acidic or basic substance for pH adjustment cannot be uniformly dispersed on biomass in the initial stage after feeding, and thus a long stirring time can be required so that a large amount of energy can be consumed.

Accordingly, the present inventors have made extensive efforts to develop a reactor capable of increasing the efficiency of mixing of an enzyme required for increasing the efficiency of saccharification of high-viscosity biomass, and as a result, have constructed a reactor for continuous saccharification of biomass, which comprises improved perforated plates and stirring means. More specifically, the present inventors have developed a reactor for continuous saccharification of biomass, in which nozzles are disposed in flow channels fluidically communicating with the inside of the holes of perforated plates such that additives, such as a saccharification enzyme, an acidic or basic substance for pH adjustment, buffer or a surfactant, can be fed to the flow channels so that the additives can be dispersed uniformly in biomass that is being finely crushed when passing through the perforated plates, and have found that, when the developed reactor is used, the efficiency of saccharification of biomass and the operational convenience of the reactor are increased.

Thus, one aspect of the present invention is directed to a reactor for continuous saccharification of high-viscosity biomass, which comprises: (a) a rotary shaft that is rotatable by separate power; (b) a plurality of stirring means fixed to the rotary shaft; (c) a cylindrical saccharification unit in which the rotary shaft passes through the central portion of the saccharification unit and the plurality of stirring means fixed to the rotary shaft are disposed at predetermined distances from one another; and (A) a plurality of perforated plates disposed between the stirring means in the cylindrical saccharification unit and configured to define a space including each of the stirring means, each of the perforated plates including one or more flow channels formed to extend from the outer circumferential surface of the perforated plate to the inside of the holes of the perforated plate, and nozzles fluidically communicating with the flow channels and the inside of the holes and configured to feed an additive.

In an embodiment of the present invention, the rotary shaft of the reactor for continuous saccharification may be disposed to pass through the central portion of the saccharification unit and to extend from the top to the bottom of the saccharification unit, and the stirring means of the saccharification unit may be attached to the rotary shaft so that they may rotate in the same direction as that of the rotary shaft to stir biomass.

The number of the stirring means disposed in the saccharification unit of the reactor for continuous saccharification may be one or more, and may be easily determined by those skilled in the art.

The perforated plates disposed in the saccharification unit of the reactor for continuous saccharification according to embodiments of the present invention may be fixedly mounted to the inner wall of the saccharification unit, or attached to the rotary shaft, or and may be configured such that it is movable upward and downward or rotatable. The perforated plates function to mix materials, and if the holes of the upper and lower perforated plates are aligned vertically, the effect of mixing can be reduced. If the perforated plates are fixed, non-mixed materials can be stagnant around the holes of the perforated plates or byproducts can be deposited. For this reason, the perforated plates are preferably rotated in order to minimize the stagnation of materials or the deposition of byproducts. In addition, if the viscosity of materials is high, the mixing and downward movement of the materials will be slow. For this reason, the perforated plates are preferably moved upward and downward in order to promote the mixing and downward movement of materials.

In embodiments of the present invention, the effect of mixing can be maximized by controlling the size, number and/or shape of the holes of the perforated plates. For example, if the size of the holes of the perforated plates is large or the number of the holes is small, the efficiency of mixing will be low, and if the size of the holes is small or the number of the holes is large, the efficiency of mixing will be high. Thus, the size or number of the holes can be selected by those skilled in the art.

In an embodiment of the present invention, the area of the holes in the reactor for continuous saccharification may be 10-90%, and preferably 50-80%, of the area of the perforated plate, and the diameter of the holes may be 0.1-100 cm. In addition, the diameter of the hole of the upper side may be 0.01-2 cm smaller than the diameter of the hole of the lower side.

The holes formed in each of the perforated plates may have the same or different sizes, and the diameter of the holes can be easily determined by those skilled in the art.

In addition, the size of the holes formed in the perforated plates may be the same or different between the perforated plates, and the diameter of the holes can be easily determined by those skilled in the art.

Thus, the perforated plates may be constructed such that the diameter of the holes of the perforated plate disposed in the upper portion of the saccharification unit may be larger than that of the holes of the perforated plate disposed in the lower portion of the saccharification unit. Feedstock is fed from the top and mixed reacted with an additive such as an enzyme as it moves to the bottom. Herein, the viscosity of feedstock in the top is high, but is reduced in the bottom as it is mixed with a reactant. For this reason, preferably, a perforated plate having a large hole size is disposed in the top in which the viscosity of feedstock is high, and a perforated plate having a small hole size is disposed in the bottom in which the viscosity of feedstock is low, so that the moving speed of feedstock will be constant. Due to this difference in the hole size, the number of the holes of the perforated plates increases toward the bottom of the saccharification unit, and thus the mixing of feedstock with an additive can more easily occur.

The shape of the holes formed in the perforated plates may be circular, square, triangular, pentagonal, hexagonal, twenty four-sided, or polygonal. In addition, holes having the same or different shapes may be formed in each of the perforated plates.

In the reactor for continuous saccharification according to embodiments of the present invention, gravity is used to move biomass in the cylindrical saccharification unit, and the perforated plates have a mixing effect. Accordingly, the number of the stirring means can be reduced, and thus the consumption of power required for rotation can be significantly reduced.

In an embodiment of the present invention, each of the perforated plates has one or more flow channels formed to extend from the outer circumferential surface of the perforated plate to the inside of the hole. Also, each perforated plate has a nozzle that communicates with each flow channel so as to feed an additive, and each perforated plate may have an additional element, such as a pH sensor or a temperature sensor, which communicates with a flow channel with which the nozzle does not communicate, in order to check the state of biomass. If the nozzle is attached to the wall of the reactor, an additive such as an enzyme will be fed to the surface of feedstock (biomass), and for this reason, the additive should be mixed with the feedstock while the feedstock moves downward by a certain distance, so that the additive will be completely mixed with the feedstock. To overcome this disadvantage, a unit for feeding an additive is frequently used in a saccharification reaction. However, this additive feeding unit acts as a factor interfering with the movement of feedstock if the feedstock has high viscosity, and thus the additive feeding unit is highly likely to be broken. For this reason, a nozzle is preferably disposed in the hole formed in the perforated plate, and the nozzle enables an additive to be uniformly fed to feedstock without interfering with the flow of the feedstock. In addition, a sensor is preferably disposed in a flow channel in which the nozzle is not disposed, in order to measure the state of feedstock.

The end of the flow channel, which is exposed through the outer circumferential surface of the perforated plate, may be connected to an additive feeding unit, a pH reader, a temperature meter or the like, but is not limited thereto.

In the reactor for continuous saccharification according to embodiments of the present invention, the nozzle and additional element may be disposed in the same perforated plate, or may be disposed in different perforated plates so that additives do not in direct contact with each other.

In the reactor for continuous saccharification according to embodiments of the present invention, the perforated plates may be disposed at predetermined distances from one another, and may be configured to define a space in which each stirring means is disposed. In addition, the kind and concentration of additive that is fed through the holes of the perforated plates may be different between the perforated plates so that the enzymatic reaction conditions will differ between the perforated plates.

In the reactor for continuous saccharification according to embodiments of the present invention, the stirring means in the saccharification unit may be one or more selected from the group consisting of a bar, a disc, a paddle and a scrapper. Preferably, the scrapper together with an additional stirring means may be disposed in each space. More preferably, the stirring means may be disposed adjacent to the top of the perforated plates, so that biomass in each space can be stirred and biomass staying on the perforated plates can be forced to move downward.

The reactor for continuous saccharification according to embodiments of the present invention is a continuous-type saccharification reactor capable of continuously treating high-viscosity biomass. Thus, it is characterized in that it reduces initial investment and has increased productivity and improved operational convenience. However, in the case of conventional bioprocesses, the concentration of a desired material is low, and thus large initial investment is required, and productivity versus equipment capacity is low.

Another aspect of the present invention is directed to a method of continuous saccharification of high-viscosity biomass, the method comprising the steps of: (a) rotating a stirring means above each of perforated plates in a saccharification unit to allow biomass to reach the perforated plate, feeding an additive to the biomass through a nozzle fluidically communicating with the inside of the hole of the perforated plate, and passing the biomass through the hole while mixing the additive with the biomass by rotation of a stirring means disposed under the perforated plate; and (b) moving the biomass downward in the saccharification unit while repeating step (a) by the perforated plates and stirring means sequentially disposed in the saccharification unit, thereby saccharifying the biomass, wherein the additive that is fed through the nozzle are at least one selected from an enzyme, an acidic or basic substance for pH adjustment and a surfactant, which are fed through different nozzles.

In an embodiment of the present invention, the perforated plate may include a pH sensor and a temperature sensor disposed in holes thereof, with which the nozzle does not communicate, in order to check the physical and chemical states of the biomass.

In an embodiment of the present invention, the enzyme and the basic substance may be fed through nozzles fluidically communicating with flow channels fluidically communicating with different holes, in order to prevent the denaturation of the enzyme.

In embodiments of the present invention, the basic substance may be sodium hydroxide (NaOH), but is not limited thereto.

In embodiments of the present invention, when biomass passes through the perforated plate during the downward movement of the biomass, the biomass can be distributed while additives, including a saccharification enzyme, fed through the nozzles, can be dispersed uniformly throughput the biomass. The biomass can be continuously mixed with the additive by the stirring means until it reaches the next perforated plate, and this mixing-stirring process is repeated until the biomass is moved to the bottom of the saccharification unit. Thus, the effect of mixing the biomass with the additive can be maximized.

In the method according to embodiments of the present invention, the enzyme is one or more selected from the group consisting of exo-glucanase, endo-glucanase, and β-glucosidase, but is not limited thereto. For example, the enzyme that can be used in embodiments of the present invention may be endo-1,3(4)-beta-glucanase, laminarinase, exo-1,2-1,6-alpha-mannosidase, alpha-N-arabinofuranosidase, feruloyl esterase, endo-1,5-alpha-arabinanase, pectinase, polygalacturonase, pectin esterase, aspartic protease, metallo protease, endo-(1,4)-mannanase, phytase, alpha-glucuronidase, beta-glucuronidase, hexenuronidase, alkaline phosphatase, acid phosphatase, alpha-galactosidase, beta-galactosidase, beta-mannosidase, and alpha-fucosidase.

In an embodiment of the present invention, exo-glucanase and/or endo-glucanase may be fed through the hole of the upper perforated plate, and β-glucosidase may be fed through the hole of the lower perforated plate.

In the continuous saccharification method according to embodiments of the present invention, when the viscosity of biomass decreases while a saccharification reaction occurs, the low-viscosity biomass is rapidly moved downward through the perforated plates, whereas the movement of biomass having a relatively high viscosity is retarded by the perforated plates. Thus, the biomass having a relatively high viscosity can be continuously mixed with an enzyme and continuously saccharified while it stays in the upper portion of the saccharification unit. Thus, according to embodiments of the present invention, the efficiency of saccharification of biomass can be increased. Thus, to facilitate the movement of biomass, the holes of perforated plates disposed in the upper portion of the reactor may have a relatively large size, and the holes of perforated plates disposed in the lower portion of the reactor may have a relatively small size. Alternatively, the size of holes in perforated plates may be different between the perforated plates to artificially control the residence time of biomass on the perforated plates, thereby maximizing the efficiency of saccharification.

Biomass that can be treated by the continuous saccharification reactor for high-viscosity biomass according to embodiments of the present invention and the method employing the same may have a solid content of 10-30 wt %.

The continuous saccharification reactor for high-viscosity biomass according to embodiments of the present invention is characterized in that a saccharification enzyme can be uniformly fed to biomass having a high solid content, and the temperature and pH during saccharification can be easily controlled.

Woody biomass is generally composed of cellulose, hemicellulose and lignin, even though the compositions and contents of the chemical components of wood vary depending on the kind of tree (a needle-leaf tree or a broad-leaved tree), the age of trees, etc. Thus, it is generally called "lignocelluloses", and is also called "cellulosic biomass", because it comprises polysaccharide cellulose that is the main component of the cell wall of woody or grassy biomass.

Thus, the term "biomass" as used herein may be used interchangeably with cellulosic biomass, woody biomass, lignocellulosic biomass or woody biomass.

Relevant types of biomasses for refining and mixing according to embodiments of the present invention may include biomasses derived from agricultural crops, for example, starch containing grains and refined starch; bagasse, straw from, for example, rice, wheat, rye, oat, barley, rye, rape, sorghum; softwood, for example, *Pinus sylvestris, Pinus radiate*; hardwood, for example, *Salix* spp. *Eucalyptus* spp.; tubers, for example, beet, potato; cereals from, for example, rice, wheat, rye, oat, barley, rye, rape, sorghum and corn; and the like.

As used herein, the term "saccharification" refers to a process in which cellulose is converted to glucose by the action of an enzyme. The saccharification process can be divided into a process in which cellulose is adsorbed onto the reactive surface of cellulose to convert cellulose to cellobiose, and a process in which the produced cellobiose is converted to glucose by the enzymatic reaction of β-glucosidase.

Unless otherwise defined, all technical terms and scientific terms as used herein have the same meanings as those generally understood by those skilled in the art to which the present invention pertains. In the following description and the accompanying drawings, the detailed description on known related functions and constructions will be omitted to avoid unnecessarily obscuring the subject matter of the present invention hereinafter.

The reactor for continuous saccharification according to embodiments of the present invention includes a plurality of perforated plates, which are at a certain distance from one another and include enzyme feeding nozzles and a sensor, which fluidically communicate with flow channels fluidically communicating with the inside of the holes of the perforated plates. Thus, biomass can be finely crushed by the perforated plates while an additive that is fed through the nozzles can be uniformly and rapidly dispersed on the biomass, and conditions for the activity of the saccharification enzyme are very easily maintained by the sensor, thereby increasing the efficiency of saccharification of biomass. Therefore, the reactor according to embodiments of the present invention is useful for the production of bio-ethanol.

What is claimed is:

1. A reactor for continuous saccharification of biomass, which comprises:
   (a) a rotary shaft that is rotatable by a power source that is separate from the reactor;
   (b) a plurality of stirring means fixed to the rotary shaft;
   (c) a cylindrical saccharification unit in which the rotary shaft passes through the central portion of the saccharification unit and the plurality of stirring means fixed to the rotary shaft are disposed at predetermined distances from one another; and
   wherein a plurality of perforated plates disposed between the stirring means in the cylindrical saccharification unit are fixed to the rotary shaft so that they can rotate in the same direction as the rotary shaft can be moved upward or downward and are configured to define a space including each of the stirring means, each of the perforated plates including one or more flow channels formed to extend from the outer circumferential surface of the perforated plate to the inside of one or more holes of the perforated plate, and nozzles fluidically communicating with the flow channels and the inside of the holes and configured to feed an additive, and
   wherein the diameter of the holes of the perforated plate disposed in an upper portion of the saccharification unit is larger than that of the holes of the perforated plate disposed in a lower portion of the saccharification unit.

2. The reactor of claim 1, wherein a diameter of the holes formed in the perforated plate is 0.1-100 cm.

3. The reactor of claim 2, wherein the holes formed in the perforated plate are configured such that difference between the diameter of the hole of an upper side and a lower side is 0.01-2 cm.

4. The reactor of claim 1, wherein the stirring means is one or more selected from the group consisting of a bar, a disc, a paddle and a scrapper.

5. The reactor of claim 4, wherein the scrapper is disposed adjacent to or in contact with the top of the perforated plates of the saccharification unit.

6. The reactor of claim 1, wherein a sensor for measuring pH or temperature is further disposed in the flow channel.

7. A method of continuous saccharification of biomass using a reactor of claim 1, the method comprising:
   (a) feeding an additive to the biomass through a nozzle fluidically communicating with the inside of a hole of a perforated plate by rotating a stirring means above each of perforated plates in a saccharification unit to allow biomass to reach the perforated plate, and mixing the additive with the biomass by rotation of a stirring means disposed under the perforated plate while passing the biomass through the hole; and
   (b) saccharifying the biomass by moving the biomass downward in the saccharification unit while repeating step (a) by the perforated plates and stirring means sequentially disposed in the saccharification unit,
   wherein the additive that is fed through the nozzle are at least one selected from an enzyme, an acidic or basic substance for pH adjustment and a surfactant, which are fed through different nozzles.

8. The method of claim 7, wherein the perforated plate without a nozzle comprises a pH sensor and a temperature sensor disposed in holes thereof, thereby checking the physical and chemical states of the biomass.

9. The method of claim 7, wherein the enzyme is one or more selected from the group consisting of exo-glucanase, endo-glucanase, and β-glucosidase.

10. The method of claim 7, wherein exo-glucanase and/or endo-glucanase is fed through the hole of the upper perforated plate, and β-glucosidase is fed through the hole of the lower perforated plate.

* * * * *

UNITED STATES PATENT AND TRADEMARK OFFICE
CERTIFICATE OF CORRECTION

PATENT NO.         : 9,976,161 B2
APPLICATION NO.    : 14/683037
DATED              : May 22, 2018
INVENTOR(S)        : Taewan Kim et al.

Page 1 of 1

It is certified that error appears in the above-identified patent and that said Letters Patent is hereby corrected as shown below:

In the Claims

Column 9, Line 19, Claim 1, after "shaft" insert -- , --

Column 9, Line 20, Claim 1, after "downward" insert -- , --

Signed and Sealed this
Twenty-first Day of August, 2018

Andrei Iancu
*Director of the United States Patent and Trademark Office*